US011828743B2

(12) United States Patent
Anderson et al.

(10) Patent No.: US 11,828,743 B2
(45) Date of Patent: Nov. 28, 2023

(54) SYSTEMS AND METHODS FOR RELIABLY DETECTING WEAR METAL PARTICLES IN LUBRICATION SYSTEMS TO AVOID PROGRESSIVE DAMAGE

(71) Applicant: Cummins Inc., Columbus, IN (US)

(72) Inventors: Travis A. Anderson, Columbus, IN (US); Neha Chandrachud, Columbus, IN (US); Renae Christianson, Columbus, IN (US); Lorraine H. Myers, Columbus, IN (US); Pallav Pathak, Columbus, IN (US); Patrick J. Shook, Franklin, IN (US)

(73) Assignee: Cummins Inc., Columbus, IN (US)

( * ) Notice: Subject to any disclaimer, the term of this patent is extended or adjusted under 35 U.S.C. 154(b) by 0 days.

(21) Appl. No.: 17/969,655

(22) Filed: Oct. 19, 2022

(65) Prior Publication Data
US 2023/0044685 A1 Feb. 9, 2023

Related U.S. Application Data

(63) Continuation of application No. 17/174,861, filed on Feb. 12, 2021, now Pat. No. 11,499,454.
(Continued)

(51) Int. Cl.
*F01M 11/10* (2006.01)
*G01N 33/28* (2006.01)

(52) U.S. Cl.
CPC ......... *G01N 33/2858* (2013.01); *F01M 11/10* (2013.01); *G01N 33/2888* (2013.01);
(Continued)

(58) Field of Classification Search
CPC ..... F01M 2011/1413; F01M 2011/144; F01M 2011/1486; G01N 33/2858; G01N 33/2864; F16N 2250/32; F16N 2250/52
See application file for complete search history.

(56) References Cited

U.S. PATENT DOCUMENTS

| 3,981,584 A | * | 9/1976 | Guymer | F01M 11/10 |
| | | | | 356/70 |
| 4,030,028 A | * | 6/1977 | Allender | G01N 15/0656 |
| | | | | 200/185 |

(Continued)

FOREIGN PATENT DOCUMENTS

| CN | 1646796 A | * | 7/2005 |
| CN | 1321260 C | * | 6/2007 |

(Continued)

OTHER PUBLICATIONS

Non-Final Office Action on U.S. Appl. No. 17/174,861 dated Mar. 2, 2022.

(Continued)

*Primary Examiner* — Kevin R Steckbauer
(74) *Attorney, Agent, or Firm* — Foley & Lardner LLP

(57) ABSTRACT

A controller includes at least one processor coupled to a memory storing instructions that, when executed by the at least one processor, cause the at least one processor to: perform operations comprising: determining a concentration of a plurality of wear metal particles in a lubricant for an engine system; determining a filtered concentration of the plurality of wear metal particles using a baseline concentration of the plurality of wear metal particles; setting a diagnostic threshold based on the filtered concentration of the wear metal particles; and, responsive to determining that the concentration of the wear metal particles exceeds the diagnostic threshold, providing a notification.

20 Claims, 4 Drawing Sheets

Related U.S. Application Data

(60) Provisional application No. 62/976,895, filed on Feb. 14, 2020.

(52) U.S. Cl.
CPC .............. *F01M 2011/144* (2013.01); *F01M 2011/1446* (2013.01); *F01M 2011/1453* (2013.01); *F01M 2011/1486* (2013.01); *F16N 2250/32* (2013.01)

(56) References Cited

U.S. PATENT DOCUMENTS

| | | | | |
|---|---|---|---|---|
| 5,049,742 | A * | 9/1991 | Hosonuma | F16N 29/00 356/70 |
| 5,070,832 | A * | 12/1991 | Hapka | F02D 17/04 123/333 |
| 5,089,780 | A * | 2/1992 | Megerle | G01N 33/2888 324/448 |
| 5,110,429 | A * | 5/1992 | Novotny | G01N 27/34 73/53.07 |
| 5,604,441 | A * | 2/1997 | Freese, V | G01N 33/2888 324/663 |
| 5,817,928 | A * | 10/1998 | Garvey, III | G01N 33/2888 324/698 |
| 6,463,796 | B1 * | 10/2002 | Van Mullekom | F01M 11/04 73/114.55 |
| 6,644,095 | B2 * | 11/2003 | Van Mullekom | F01M 11/06 73/10 |
| 7,370,514 | B2 * | 5/2008 | Halalay | G01N 33/2888 73/53.05 |
| 7,385,694 | B2 * | 6/2008 | Kolp | G01N 15/147 356/335 |
| 7,523,646 | B2 * | 4/2009 | Klun | G01N 33/2888 73/53.07 |
| 7,581,434 | B1 * | 9/2009 | Discenzo | G01N 33/2888 73/53.01 |
| 7,917,307 | B2 * | 3/2011 | Bolt | G01N 33/2888 702/182 |
| 8,522,604 | B2 * | 9/2013 | Zhe | G01M 13/02 73/53.07 |
| 8,965,625 | B2 * | 2/2015 | Dvorak | F01M 11/10 701/29.5 |
| 8,977,421 | B2 * | 3/2015 | Dvorak | G01N 33/2888 701/29.5 |
| 9,205,845 | B2 * | 12/2015 | Uluyol | B60W 50/00 |
| 9,389,215 | B2 * | 7/2016 | Von Herzen | G01N 33/2888 |
| 9,488,633 | B2 * | 11/2016 | Atkinson | G01N 31/22 |
| 9,568,461 | B2 * | 2/2017 | Von Herzen | F01M 11/10 |
| 9,588,097 | B2 * | 3/2017 | Rohde | G01N 33/2858 |
| 9,651,537 | B2 * | 5/2017 | De Coninck | G01N 29/02 |
| 9,651,538 | B2 * | 5/2017 | Von Herzen | G01N 33/28 |
| 10,018,613 | B2 * | 7/2018 | Potyrailo | G01N 33/2888 |
| 10,254,270 | B2 * | 4/2019 | Potyrailo | G01M 13/021 |
| 10,260,388 | B2 * | 4/2019 | Potyrailo | G01N 33/2847 |
| 10,409,275 | B2 * | 9/2019 | Hagen | G05B 23/0289 |
| 10,539,524 | B2 * | 1/2020 | Potyrailo | G01N 33/2847 |
| 10,619,533 | B2 * | 4/2020 | Barnes | F02D 41/26 |
| 10,746,680 | B2 * | 8/2020 | Potyrailo | G01N 27/026 |
| 10,818,107 | B2 * | 10/2020 | Mentele | G07C 5/0808 |
| 11,209,357 | B2 * | 12/2021 | Kojima | G01N 21/51 |
| 11,499,454 | B2 * | 11/2022 | Anderson | F01M 11/10 |
| 2002/0178780 | A1 * | 12/2002 | Van Mullekom | F01M 11/10 73/10 |
| 2006/0232267 | A1 * | 10/2006 | Halalay | G01N 33/2888 508/110 |
| 2007/0040559 | A1 * | 2/2007 | Klun | G01N 33/03 324/453 |
| 2010/0036619 | A1 * | 2/2010 | Bolt | G01N 33/2888 702/50 |
| 2010/0109686 | A1 * | 5/2010 | Zhe | G01N 33/2888 324/698 |
| 2010/0126251 | A1 * | 5/2010 | Pileggi | G01N 33/2888 73/53.07 |
| 2013/0080085 | A1 * | 3/2013 | Von Herzen | G01N 33/30 702/50 |
| 2013/0197738 | A1 * | 8/2013 | Dvorak | G01N 33/2858 701/29.5 |
| 2014/0083172 | A1 * | 3/2014 | Rohde | G01N 33/2858 73/53.05 |
| 2014/0130587 | A1 * | 5/2014 | Von Herzen | G01N 33/2888 73/114.55 |
| 2014/0188404 | A1 * | 7/2014 | Von Herzen | F16N 29/00 702/31 |
| 2014/0188407 | A1 * | 7/2014 | Von Herzen | G01N 33/28 702/50 |
| 2014/0266065 | A1 * | 9/2014 | Von Herzen | G01N 33/2888 320/167 |
| 2014/0343786 | A1 * | 11/2014 | Dvorak | F01M 11/10 702/50 |
| 2014/0365144 | A1 * | 12/2014 | Dvorak | F01M 11/04 702/50 |
| 2015/0160179 | A1 * | 6/2015 | Atkinson | G01N 33/22 436/60 |
| 2015/0192558 | A1 * | 7/2015 | De Coninck | G01N 29/022 73/61.49 |
| 2016/0003794 | A1 * | 1/2016 | Basu | G01N 33/2888 702/30 |
| 2016/0018381 | A1 * | 1/2016 | Potyrailo | G01N 27/026 324/633 |
| 2016/0054291 | A1 * | 2/2016 | O'Donnell | G01N 25/00 702/22 |
| 2016/0187277 | A1 * | 6/2016 | Potyrailo | G01N 27/026 324/633 |
| 2016/0195509 | A1 * | 7/2016 | Jamieson | G01N 21/718 356/70 |
| 2016/0363575 | A1 * | 12/2016 | Von Herzen | G01N 33/2888 |
| 2017/0081997 | A1 * | 3/2017 | Potyrailo | F01M 11/12 |
| 2017/0138876 | A1 * | 5/2017 | Potyrailo | G01N 33/2847 |
| 2017/0138922 | A1 * | 5/2017 | Potyrailo | G01N 33/2888 |
| 2017/0183992 | A1 * | 6/2017 | Barnes | F01M 11/10 |
| 2017/0248572 | A1 * | 8/2017 | Byington | G01N 33/2888 |
| 2018/0017541 | A1 * | 1/2018 | Kinard | G01N 33/2888 |
| 2018/0107203 | A1 * | 4/2018 | Hagen | F16N 29/00 |
| 2018/0158261 | A1 * | 6/2018 | Ottikkutti | G01N 33/2888 |
| 2018/0187622 | A1 * | 7/2018 | Rudolecky | F01M 11/10 |
| 2018/0231518 | A1 * | 8/2018 | Vaidya | F01M 11/10 |
| 2019/0187036 | A1 * | 6/2019 | Barraclough | G01N 15/0266 |
| 2019/0304214 | A1 * | 10/2019 | Mentele | G07C 5/0825 |
| 2020/0018200 | A1 * | 1/2020 | Vaidya | F01M 1/10 |
| 2020/0142392 | A1 * | 5/2020 | Prabhu | G05B 23/0294 |
| 2020/0292450 | A1 * | 9/2020 | Kojima | G01N 21/78 |
| 2020/0325657 | A1 * | 10/2020 | Takami | G05B 23/0259 |
| 2020/0355163 | A1 * | 11/2020 | Kojima | F03D 17/00 |
| 2020/0409349 | A9 * | 12/2020 | Prabhu | G05B 13/048 |
| 2021/0033552 | A1 * | 2/2021 | Potyrailo | G01N 33/2888 |
| 2021/0254519 | A1 * | 8/2021 | Anderson | F01M 11/10 |
| 2021/0260585 | A1 * | 8/2021 | Alabi | G01N 33/2888 |
| 2021/0381641 | A1 * | 12/2021 | Nitsche | G01N 33/30 |
| 2022/0018825 | A1 * | 1/2022 | Tabata | F15B 19/00 |
| 2022/0065142 | A1 * | 3/2022 | Shah | F01M 11/12 |
| 2022/0074840 | A1 * | 3/2022 | Monden | G01N 33/2835 |

FOREIGN PATENT DOCUMENTS

| | | | |
|---|---|---|---|
| CN | 102818754 A | * | 12/2012 |
| CN | 103675241 A | * | 3/2014 |
| CN | 102818754 B | * | 8/2014 |
| CN | 107524493 A | * | 12/2017 |
| CN | 110907626 A | * | 3/2020 |
| CN | 110907626 B | * | 6/2020 |
| CN | 112505303 A | * | 3/2021 |
| CN | 113944746 A | * | 1/2022 |
| CN | 114199583 A | * | 3/2022 |
| DE | 10 2021 201 345 A1 | | 8/2021 |
| DE | 102021201345 A1 | * | 8/2021 |
| DE | 102021118213 A1 | * | 1/2022 .......... F15B 19/00 |
| EP | 2 711 702 A1 | | 3/2014 |
| EP | 2711702 A1 | * | 3/2014 |

(56) References Cited

FOREIGN PATENT DOCUMENTS

| EP | 3964703 A1 * | 3/2022 | |
|----|---|---|---|
| FR | 2941909 A1 * | 8/2010 | |
| JP | 2021-017862 A | 2/2021 | |
| JP | 2021017862 A * | 2/2021 | |
| JP | 2022019043 A * | 1/2022 | .............. F15B 19/00 |
| WO | WO-01/08924 A1 | 2/2001 | |
| WO | WO-0108924 A1 * | 2/2001 | |
| WO | WO-0231323 A1 * | 4/2002 | |
| WO | WO-2008/052890 A2 | 5/2008 | |
| WO | WO-2008052890 A2 * | 5/2008 | |
| WO | WO-2018/056950 A1 | 3/2018 | |
| WO | WO-2018056950 A1 * | 3/2018 | |
| WO | WO-2020002946 A1 * | 1/2020 | ......... B01D 11/0496 |

OTHER PUBLICATIONS

Notice of Allowance on U.S. Appl. No. 17/174,861 dated Jul. 14, 2022.

* cited by examiner

SYSTEMS AND METHODS FOR RELIABLY DETECTING WEAR METAL PARTICLES IN LUBRICATION SYSTEMS TO AVOID PROGRESSIVE DAMAGE

CROSS-REFERENCE TO RELATED APPLICATIONS

This application is a continuation of U.S. patent application Ser. No. 17/174,861, filed on Feb. 12, 2021, and titled "SYSTEMS AND METHODS FOR RELIABLY DETECTING WEAR METAL PARTICLES IN LUBRICATION SYSTEMS TO AVOID PROGRESSIVE DAMAGE," which claims the benefit of and priority to U.S. Pat. App. No. 62/976,895, titled "SYSTEMS AND METHODS FOR RELIABLY DETECTING WEAR METAL PARTICLES IN LUBRICATION SYSTEMS TO AVOID PROGRESSIVE DAMAGE", filed Feb. 14, 2020, both of which are incorporated herein by reference in their entireties and for all purposes.

TECHNICAL FIELD

The present disclosure relates to a wear metal detection system for identifying a presence and a size of wear metal particles in a lubricant (e.g., oil for an engine).

BACKGROUND

Internal combustion engines generally include a lubrication system that circulates lubricant (e.g., oil, synthetic oil, etc.) to the moving parts of the internal combustion engine (e.g., pistons moving within cylinders). Sometimes, small pieces of metal are produced by the motion of these parts. These particles can cause wear damage and extra friction in between the surfaces of the moving parts, which can cause various issues with these parts, such as raising surface temperatures and causing even more particles to be created.

SUMMARY

One embodiment relates to a system. The system includes a controller comprising at least one processor coupled to a memory storing instructions that, when executed by the at least one processor, cause the at least one processor to: determine a concentration of a plurality of wear metal particles in lubricant of an engine system; determine a confidence parameter regarding the reliability of the concentration determination; determine a filtered concentration of the plurality of wear metal particles using a baseline concentration of the plurality of wear metal particles; set a diagnostic threshold for the plurality of wear metal particles; and, responsive to determining that the diagnostic threshold is exceeded, provide a notification.

Another embodiment relates to a method. The method includes: determining, by a controller, a concentration of a plurality of wear metal particles in a lubricant for an engine system; determining, by the controller, a confidence parameter regarding the concentration determination; determining, by the controller, a filtered concentration of the plurality of wear metal particles using a baseline concentration of the plurality of wear metal particles; setting, by the controller, a diagnostic threshold for the plurality of wear metal particles based on the confidence parameter; and, responsive to determining that the diagnostic threshold is exceeded, providing, by the controller, a notification.

Another embodiment relates to a controller. The controller includes a processing circuit having at least one processor coupled to at least one memory device, the processing circuit configured to execute a plurality of circuits including: a concentration circuit structured to determine a concentration of a plurality of wear metal particles in a lubricant for an engine system; a confidence circuit structured to determine a confidence parameter regarding the concentration determination; a baselining circuit structured to determine a filtered concentration of the plurality of wear metal particles using a baseline concentration of the plurality of wear metal particles; a dynamic threshold circuit structured to set a diagnostic threshold for the plurality of wear metal particles based on the confidence parameter; and a notification circuit structured to responsive to determining that the diagnostic threshold is exceeded, provide a notification.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
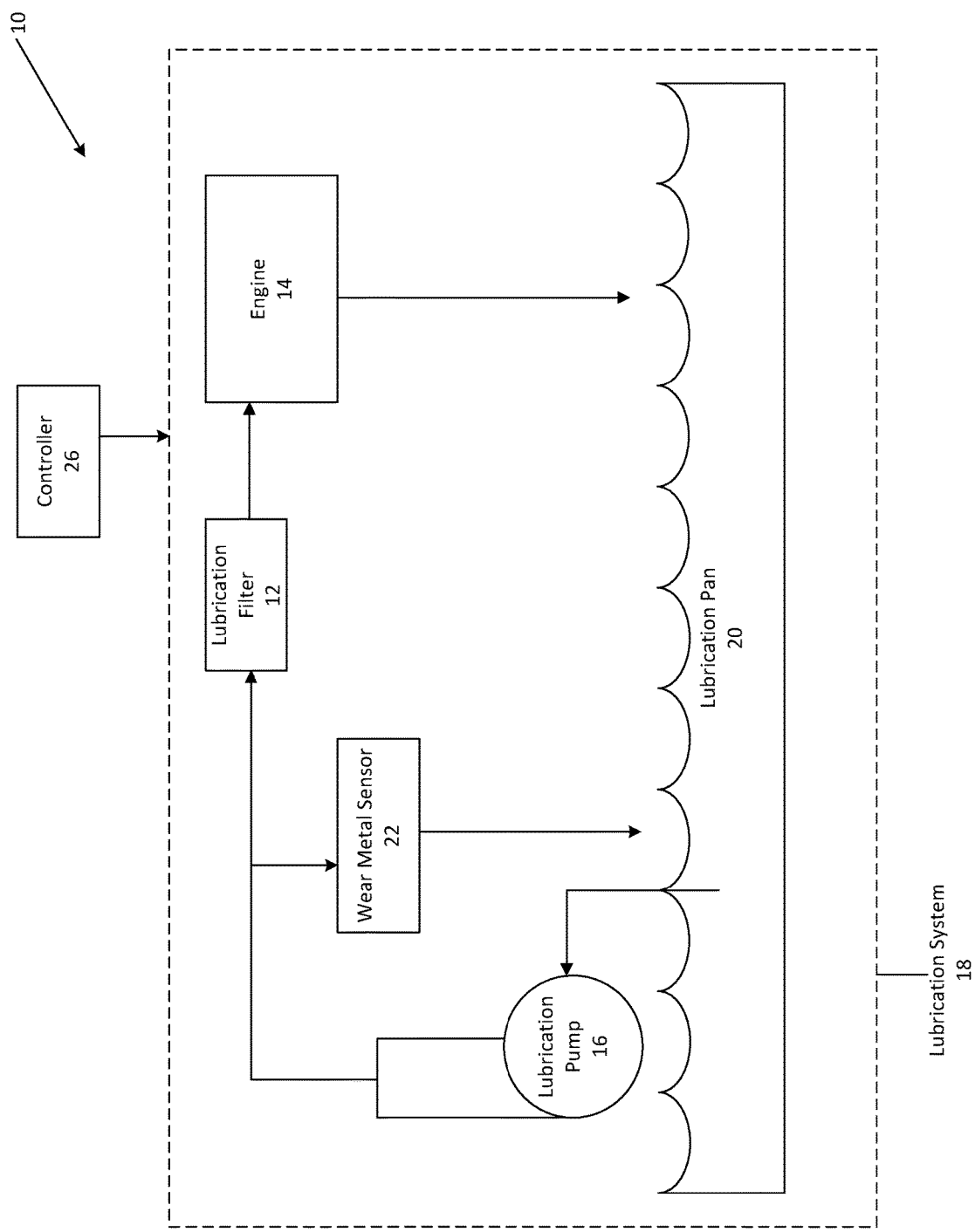
FIG. 1 is a schematic diagram of an engine system, according to an example embodiment.

Following below are more detailed descriptions of various concepts related to, and implementations of, methods, apparatuses, and systems for utilizing a wear metal sensor to identify a presence and a size of wear metal particles in a lubricant for an engine. Before turning to the Figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting. In particular, although the specification refers to oil as being the lubricant used in exemplary embodiments, the systems and methods, as described herein, should not be read as limited to oil and should be read as applicable to other lubricants utilized with and in engines.

Referring to the Figures generally, the various embodiments disclosed herein relate to systems, apparatuses, and methods for utilizing a wear metal sensor and a controller to identify the presence and size of wear metal particles. A lubrication system for an engine may include a pump, a pressure regulation device, a filter, flow paths of lubricant to various components of the engine, and a return flow path for returning the lubricant to a temporary storage location, such as a sump or a pan, where the lubricant waits to be pumped again. In many modern engines, the filter will remove most, if not all, particles larger than a specified size. Engine systems include many lubricated parts, such as piston rings, cylinder liners, various journal and rolling element bearings, gear teeth, and cam tappets, rollers, and lobes. These parts are lubricated to reduce friction as the parts move during use. Further, many of these parts have very small clearance spaces to move. For example, a cylindrical journal surface with an outer diameter of 100.00 mm may rotate in a stationary mounted bearing with an inside diameter of 100.05 mm. Sometimes, small pieces, or particles, of metal are produced by the motion of these parts. This is especially true when parts are very new and are being broken-in, when manufacturing errors or tolerance extremes create unexpectedly small clearances, and/or when maintenance is poor, which results in not enough or highly degraded lubricant being applied to the surface of these parts.

As these pieces of metal are generated, the pieces of metal are generally picked up by the nearby flowing lubricant and carried to the oil pan. Here, the pieces of metal are picked up by the pump and sent toward the lube filter, which traps the particles. If, however, the quantity of the metal particles is such that the lubricant cannot carry them away or they somehow pass through the filter, the particles can remain near the surfaces in motion thereby causing wear damage and extra friction in the joint. In turn, this can raise surface temperatures, which could damage and overheat components, such as bearings, and cause even more particles to be created. The damage caused by these pieces of metal can cascade and increase in scale quickly as the affected area grows in size. If not treated quickly, the wear metal pieces can cause the lubricant to degrade more quickly in the high temperatures produced by the increased friction and can lead to an increase in blow-by due to wear in the lubricated surfaces. Further, these wear metal particles can cause the engine parts to become fatigued, which could lead to seizure of parts and failure of the engine.

According to the present disclosure, a wear metal sensor tracks or facilitates tracking of wear metal particles as the lubricant flows from the lube pump towards the lube filter. Through tracking the particles, the controller determines various properties or characteristics of the particles (e.g., the size, a count of particles, whether or not the particles are ferrous (i.e. whether the particles contain iron or do not contain iron), etc.). The controller also tracks the volume of oil flowing. Utilizing this volume, the controller determines or calculates the concentration of particles over a time interval. This concentration of wear metal particles may be monitored using a size bin methodology in order to determine if preset or predefined particle rate limits have been exceeded. When at or above the predefined limit, the controller notifies the driver or another user/monitor that there is an unacceptably high concentration of wear metal particles in the lubricant. The controller may also provide a list of suggested actions, such as replacing parts, de-rating the engine, or even complete engine shutdown. In some embodiments, the controller performs these suggested actions automatically, such as by ordering replacement parts or immediately de-rating the engine. By either providing this notification and suggested actions or acting automatically, the controller lowers the risk of severe damage to the engine and reduces the length and cost of down-time.

These particle rate limits may be dynamic in response to various factors, such as recentness of engine service (e.g. more recent engine service may correspond with relatively higher thresholds to account for newer engine parts with rough edges that have not yet been broken-in) or of engine start. In addition, the concentration values themselves may be adjusted through a baselining technique, which adjusts the time interval for calculating concentration in coordination with a calculated parameter for confidence. Further, a cumulative summation (Cusum) methodology may be employed in order to account for system noise. Employing a Cusum function serves to pace the controller so that it is not responding with a false fault the instant that a diagnostic threshold is exceeded. These dynamic elements reduce false faults during times when the algorithm has information which is too new or too variable. False faults in this situation can be very expensive. When an alert is triggered due to increased presence of wear metal particles, the engine is typically shut down, lubricant is removed for sampling, and parts, such as the especially cumbersome main bearing caps, are taken off of the engine for inspection. There is a technical advantage to incorporating dynamic limits in the system by improving system reliability and reducing the chances of a false fault.

By utilizing the controller and wear metal sensor to identify the presence and size of wear metal particles in the lubricant in real-time or near real-time, the engine can be protected from progressive damage to components like the cylinder block, gear train, connecting rod, main bearings, fuel pumps, cam followers, lobes, and tappets, that would otherwise be caused by the excess metal particles. In this regard, a reduction in unscheduled machine downtime, help with ordering replacement components when needed, and a determination if maintenance was properly completed at a prior service visit may be realized.

Despite being primarily discussed herein with respect to being applicable with engine and engine systems, it should be understood that the systems and the methods described herein are equally applicable to any lubricated component that may generate wear metal particles, such as a gearbox, transmission, hydraulic pump, etc.

Figure 2:
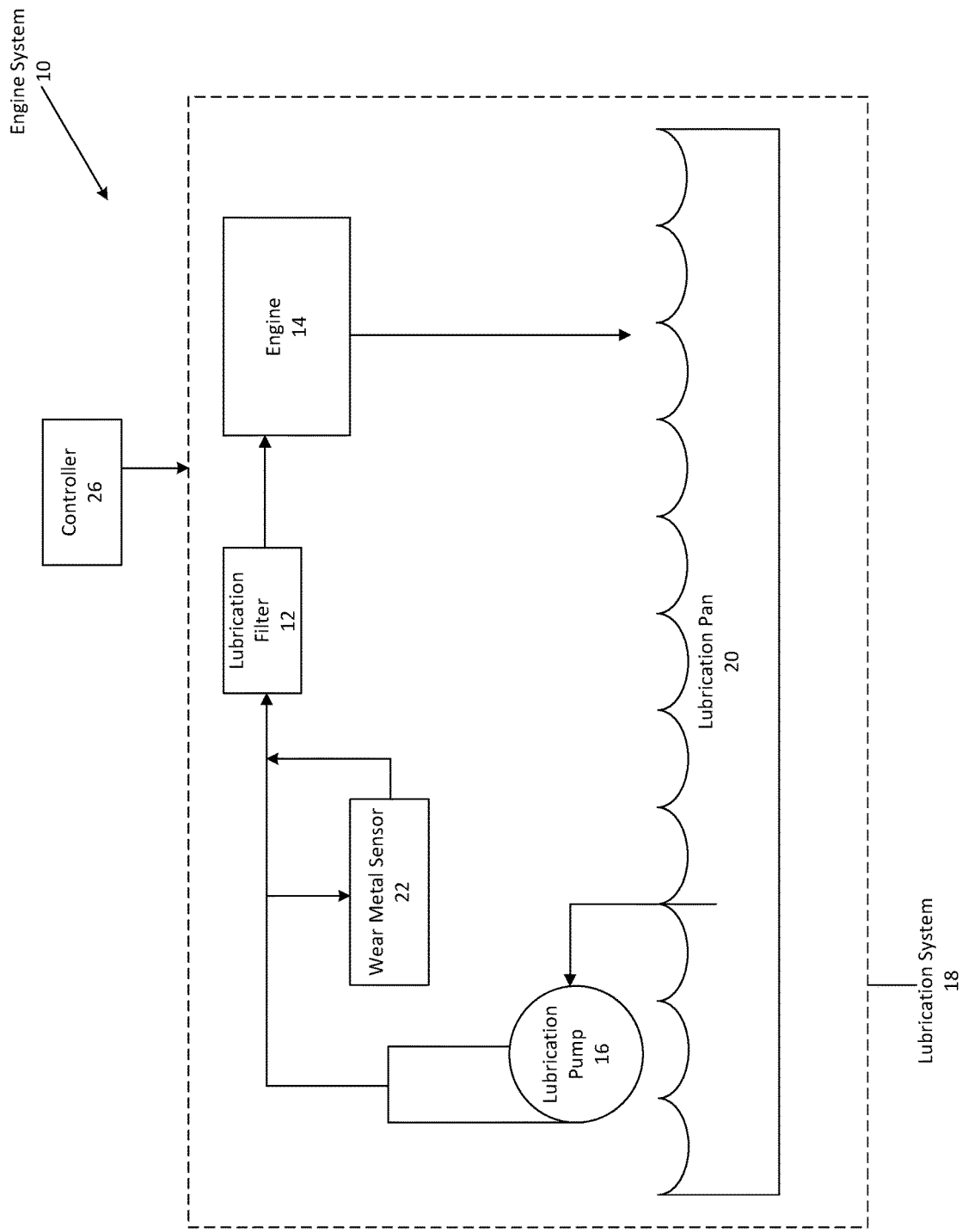
FIG. 2 is a schematic diagram of an engine system, according to another embodiment.

Referring now to FIGS. 1 and 2, exemplary architectures for engine systems are shown. These schematics are intended to depict different relative locations of a wear metal detection sensor. FIGS. 1 and 2 depict two such architectures. Similar reference numbers are utilized to identify similar components.

Referring first to FIG. 1, an engine system 10 with a lubrication system 18 and a controller 26 is shown, according to an example embodiment. The engine system 10 includes an engine 14, which may be any type of engine. In the example shown, the engine 14 is a diesel engine utilizing compression-ignition. In other embodiments, different engine configurations are possible, such as a spark-ignition engine. According to one embodiment, the engine system 10 is embodied within a vehicle. The vehicle may include an on-road or an off-road vehicle including, but not limited to, line-haul trucks, mid-range trucks (e.g., pick-up truck, etc.), sedans, coupes, tanks, airplanes, boats, and any other type of vehicle. In some embodiments, the engine system 10 may be implemented in stationary devices, such as a power generator. Based on these configurations, various additional types of components may also be included in the system, such as a transmission, one or more gearboxes, pumps, actuators, and so on.

A lubrication system 18 is coupled to the engine 14. The lubrication system 18 includes a lubrication filter 12, a lubrication pump 16, a lubrication pan 20, and a wear metal sensor 22. The lubrication filter 12 receives lubricant from the lubrication pump 16 and filters the lubricant to remove unwanted particles from the lubricant before flowing to the engine 14. The lubrication pump 16 is a pump structured to draw a lubricant from the lubrication pan 20 and send the lubricant through tubing to the engine 14. The lubrication pan 20 is a reservoir structured to receive unutilized lubricant from the engine 14 and hold the lubricant until it is drawn by the lubrication pump 16. As the lubrication system 18 operates, lubricant (in this example, oil) starts out in the lubrication pan 20 and is pumped by the lubrication pump 16 to the engine 14. A small sample of the pumped oil is routed to the wear metal sensor 22, after which it returns to the lubrication pan 20. The majority of the oil goes through the lubrication filter 12 and then to the engine 14. Unutilized oil may be returned to the lubrication pan 20.

Referring now to FIG. 2 and in this architecture, the oil that is routed to the wear metal sensor 22 is returned to the primary flow and passes through the lubrication filter 12 to be used with the engine 14 alongside the untested oil, according to an alternative embodiment. This parallel flow structure avoids instances in which the wear metal sensor 22 is sensing the same wear metal particles each pass. Because the tested oil is then passing through the lubrication filter 12, sensed wear metal particles are being removed from the oil so those wear metal particles would not remain in the oil to be sensed a second time.

The wear metal sensor 22 of FIGS. 1 and 2 may be one or more sensors arranged to measure or otherwise acquire data, values, or information regarding attributes of the engine 14 and the lubrication system 18. In the situation where multiple sensors are utilized, the multiple sensors may be all real sensors, all virtual sensors, or a combination thereof. In some embodiments, the wear metal sensor 22 is a particle sensor (e.g. wear metal detection sensor, wear metal debris sensor, etc.) structured to send a signal to the controller 26 indicative of the amount and type of wear metal particles in the lubricant flow or of the type of wear metal particles, either ferrous or non-ferrous. For example, the wear metal sensor 22 may be or include an inductive proximity sensor that senses metal such that the controller may distinguish between ferrous and non-ferrous particles (e.g., distinguish between types of metallic particles). In some embodiments, the wear metal sensor 22 is or includes a flow sensor structured to send a signal to the controller 26 indicative of the quantity, speed, and/or pressure of the lubricant flow as it is routed into the wear metal sensor 22, as shown in FIG. 1. The engine system 10 is structured to divert a certain portion of the lubricant flow to the wear metal sensor 22. In some embodiments, the quantity of this certain portion is fixed at a relatively low value in order to avoid overwhelming the limited capacity of the wear metal sensor 22. Alternatively, the wear metal sensor 22 and controller 26 are structured to communicate with each other regarding the wear metal sensor 22 capacity so that the controller 26 can alter or adjust the flow diversion in response to readings from the wear metal sensor 22.

The controller 26 is structured to at least partly control the engine 14 and the lubrication system 18. The controller 26 is coupled with the wear metal sensor 22 and receives signals therefrom. The controller 26 uses the signals received from the wear metal sensor 22 to determine wear metal particle severity and perform actions in response.

As the components of FIGS. 1 and 2 are shown to be embodied in the engine system 10, the controller 26 may be structured as one or more electronic control units (ECU). The controller 26 may be separate from or included with at least one of a transmission control unit, an exhaust aftertreatment control unit, a powertrain control module, an engine control module, etc. The function and structure of the controller 26 is described in greater detail in FIG. 3.

Figure 3:
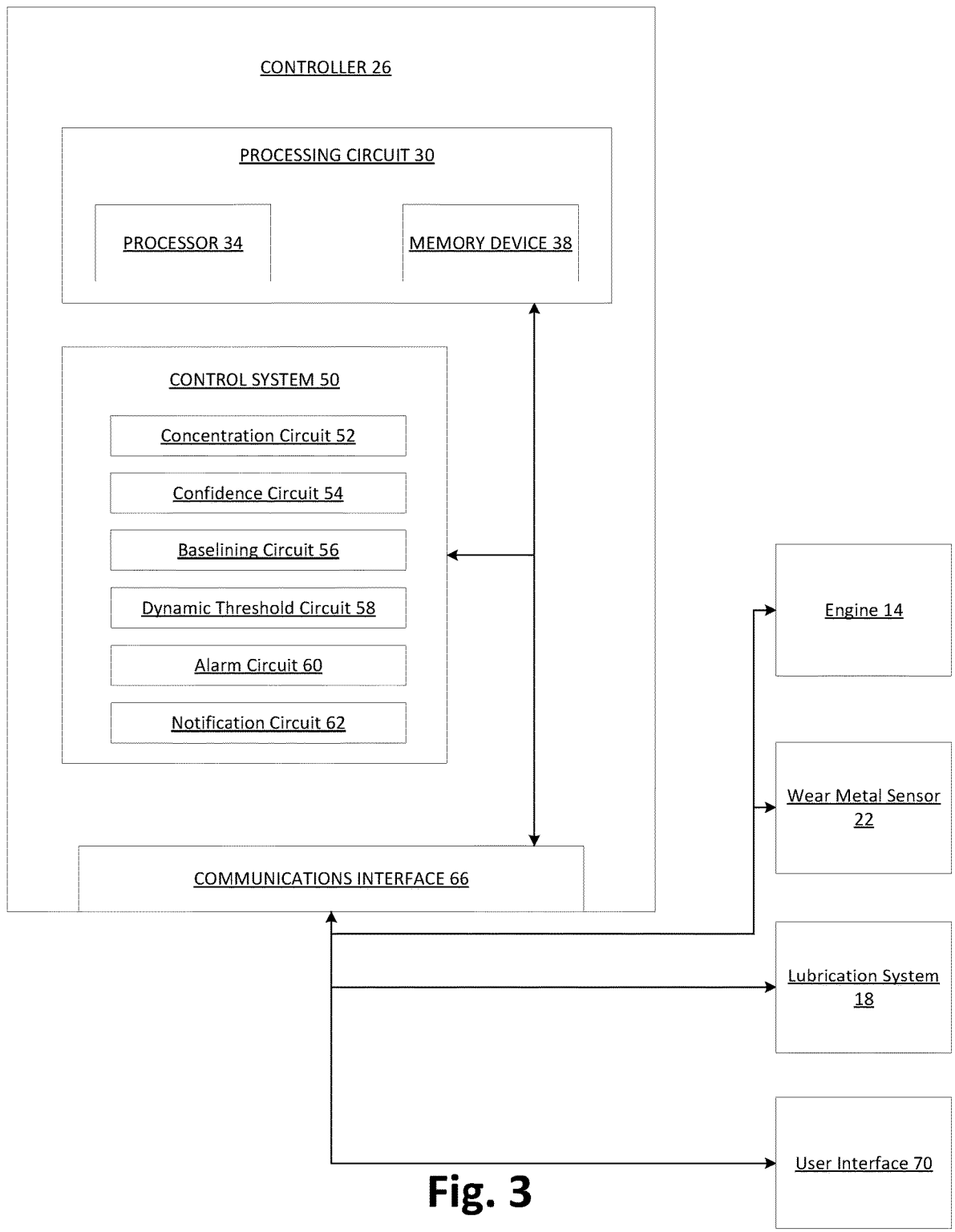
FIG. 3 is a schematic view of a controller of the engine system of FIGS. 1 and 2, according to an example embodiment.

Referring now to FIG. 3, a schematic diagram of the controller 26 of the engine system 10 of FIGS. 1-2 is shown, according to an example embodiment. As shown in FIG. 3, the controller 26 includes a processing circuit 30 having a processor 34 and a memory device 38, a control system 50 having a concentration circuit 52, a confidence circuit 54, a baselining circuit 56, a dynamic threshold circuit 58, an alert circuit 60, a notification circuit 62, and a communications interface 66. The controller 26 is structured to communicate with the control system 50 in order to regulate and set the engine system 10 performance in response to output from the circuits of the control system 50.

In one configuration, the concentration circuit 52, the confidence circuit 54, the baselining circuit 56, the dynamic threshold circuit 58, the alert circuit 60, and the notification circuit 62 are embodied as machine or computer-readable media that is executable by a processor, such as processor 34. As described herein and amongst other uses, the machine-readable media facilitates performance of certain operations to enable reception and transmission of data. For example, the machine-readable media may provide an instruction (e.g., command, etc.) to, e.g., acquire data. In this regard, the machine-readable media may include programmable logic that defines the frequency of acquisition of the data (or, transmission of the data). The computer readable media may include code, which may be written in any programming language including, but not limited to, Java or the like and any conventional procedural programming languages, such as the "C" programming language or similar programming languages. The computer readable program code may be executed on one processor or multiple remote processors. In the latter scenario, the remote processors may be connected to each other through any type of network (e.g., CAN bus, etc.).

In another configuration, the concentration circuit 52, the confidence circuit 54, the baselining circuit 56, the dynamic threshold circuit 58, the alert circuit 60, and the notification circuit 62 are embodied as hardware units, such as electronic control units. As such, the concentration circuit 52, the confidence circuit 54, the baselining circuit 56, the dynamic threshold circuit 58, the alert circuit 60, and the notification circuit 62 may be embodied as one or more circuitry components including, but not limited to, processing circuitry, network interfaces, peripheral devices, input devices, output devices, sensors, etc. In some embodiments, the concentration circuit 52, the confidence circuit 54, the baselining circuit 56, the dynamic threshold circuit 58, the alert circuit 60, and the notification circuit 62 may take the form of one or more analog circuits, electronic circuits (e.g., integrated circuits (IC), discrete circuits, system on a chip (SOCs) circuits, microcontrollers, etc.), telecommunication circuits, hybrid circuits, and any other type of "circuit." In this regard, the concentration circuit 52, the confidence circuit 54, the baselining circuit 56, the dynamic threshold circuit 58, the alert circuit 60, and the notification circuit 62 may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on). The concentration circuit 52, the confidence circuit 54, the baselining circuit 56, the dynamic threshold circuit 58, the alert circuit 60, and the notification circuit 62 may also include programmable hardware devices such as field programmable gate arrays, programmable array logic, programmable logic devices or the like. The concentration circuit 52, the confidence circuit 54, the baselining circuit 56, the dynamic threshold circuit 58, the alert circuit 60, and the notification circuit 62 may include one or more memory devices for storing instructions that are executable by the processor(s) of the concentration circuit 52, the confidence circuit 54, the baselining circuit 56, the dynamic threshold circuit 58, the alert circuit 60, and the notification circuit 62. The one or more memory devices and processor(s) may have the same definition as provided below with respect to the memory device 38 and processor 34. In some hardware unit configurations, the concentration circuit 52, the confidence circuit 54, the baselining circuit 56, the dynamic threshold circuit 58, the alert circuit 60, and the notification circuit 62 may be geographically dispersed throughout separate locations in the vehicle. Alternatively and as shown, the concentration circuit 52, the confidence circuit 54, the baselining circuit 56, the dynamic threshold circuit 58, the alert circuit 60, and the notification circuit 62 may be embodied in or within a single unit/housing, which is shown as the controller 26.

In the example shown, the controller 26 includes the processing circuit 30 having the processor 34 and the memory device 38. The processing circuit 30 may be structured or configured to execute or implement the instructions, commands, and/or control processes described herein with respect to concentration circuit 52, the confidence circuit 54, the baselining circuit 56, the dynamic threshold circuit 58, the alert circuit 60, and the notification circuit 62. The depicted configuration represents the concentration circuit 52, the confidence circuit 54, the baselining circuit 56, the dynamic threshold circuit 58, the alert circuit 60, and the notification circuit 62 as machine or computer-readable media. However, as mentioned above, this illustration is not meant to be limiting as the present disclosure contemplates other embodiments where the concentration circuit 52, the confidence circuit 54, the baselining circuit 56, the dynamic threshold circuit 58, the alert circuit 60, and the notification circuit 62, or at least one circuit of the concentration circuit 52, the confidence circuit 54, the baselining circuit 56, the dynamic threshold circuit 58, the alert circuit 60, and the notification circuit 62, is configured as a hardware unit. All such combinations and variations are intended to fall within the scope of the present disclosure.

The hardware and data processing components used to implement the various processes, operations, illustrative logics, logical blocks, modules and circuits described in connection with the embodiments disclosed herein (e.g., the processor 34) may be implemented or performed with a single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. The processor may be a microprocessor, or, any conventional processor, or state machine. A processor also may be implemented as a combination of computing devices, such as a combination of a DSP and a microprocessor, a plurality of microprocessors, one or more microprocessors in conjunction with a DSP core, or any other such configuration. In some embodiments, the one or more processors may be shared by multiple circuits (e.g., concentration circuit 52, the confidence circuit 54, the baselining circuit 56, the dynamic threshold circuit 58, the alert circuit 60, and the notification circuit 62 may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. All such variations are intended to fall within the scope of the present disclosure.

The memory device 38 (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory device 38 may be communicably connected to the processor 34 to provide computer code or instructions to the processor 34 for executing at least some of the processes described herein. Moreover, the memory device 38 may be or include tangible, non-transient volatile memory or non-volatile memory. Accordingly, the memory device 38 may include database components, object code components, script components, or any other type of information structure for supporting the various activities and information structures described herein.

The concentration circuit 52 is structured to communicate with the wear metal sensor 22 via the communications interface 66, sort the wear metal particles by various sensed characteristics, and calculate or otherwise determine a concentration of wear metal particles per unit of lubricant flow volume. Based on data from the wear metal sensor 22, the concentration circuit 52 may process a portion of the lubricant flow in the engine system 10 over a specified time interval to determine at least one property of the wear metal particles contained in the lubricant, such as particle type (i.e. ferrous or non-ferrous), particle size, and quantity of wear metal particles. Based on this determination and sorting, the concentration circuit 52 separates the counted particles into groupings. In some embodiments, these groupings are discrete size ranges that are categorized according to predefined parameter 'bins'. In some embodiments, these defined parameters are size ranges (i.e. a bin for particles measuring 20-40 µm, a bin for particles measuring 40-80 µm, etc.). In some other embodiments, the defined parameters are type of particle (i.e., a bin for ferrous particles, a bin for non-ferrous particles). In yet further embodiments the defined parameters may be any combination thereof (i.e., a bin for ferrous particles measuring 20-40 µm, a bin for non-ferrous particles measuring 20-40 µm, etc.).

After separating the counted particles into bins, the concentration circuit 52 receives, from the wear metal sensor 22, the measured volume of the lubricant that had passed through the wear metal sensor 22 during the specified time interval. Alternatively, the concentration circuit 52 may determine the volume of lubricant that has passed through or otherwise engaged with the wear metal sensor 22 over a predefined time interval. In this embodiment, a timer may be utilized to keep track of the interval and flow data from the wear metal sensor 22 is used in combination to determine the volume of lubricant per unit of specified time. The concentration circuit 52 then divides each bin by the measured volume of lubricant to determine the concentration of wear metal particles per unit of lubricant flow volume for the specified time interval.

The confidence circuit 54 is structured to reduce false faults by modifying diagnostic thresholds. For example, the confidence circuit 54 may reduce false faults when information is received indicating that parts have just been replaced and may have too much variation to be reliable. In this regard, some parts in the engine 14 may have been serviced while the engine system 10 and controller 26 were turned off, so the readings from the wear metal sensor 22 may not line up with what the controller 26 is expecting at engine start up because the replacement parts are not yet 'broken-in.' In some embodiments, the confidence is calculated based on a service timer value regarding a time since the last service of the engine and, in some embodiments, since the lubricant was last changed (i.e., a service event). The time may be in hours, miles, etc. A time reset, in these embodiments, may occur when the service technician sets the timer back to zero. In other of these embodiments, the controller 26 may automatically set the timer back to zero if it detects that a service of the engine system 10 has occurred. In these embodiments, the confidence value grows higher as the service timer value increases, indicating that the confidence circuit 54 has more confidence in the reliability of the wear metal sensor 22 readings as the changes incorporated by the engine service are or more likely are fully integrated into the engine system 10.

In further embodiments, the confidence parameter is calculated or determined based on an engine timer value regarding a time of on-time for the engine system 10 (e.g., hours, miles, days, etc.). In some of these embodiments, this time of on-time for the engine system 10 is based on the last time the engine system 10 was started (i.e. the most recent keying-on event). In other of these embodiments, the time of on-time for the engine system 10 is based on the first time the engine system 10 was ever started. In some of these embodiments, the timer may wait to start until the enable conditions for the confidence circuit 54 are ready (e.g. wear metal sensor 22 readings are being received, engine 14 is running, etc.). For instance, if the engine 14 is keyed on but is not running, the engine timer will not start. In these embodiments, the confidence value grows higher as the engine time value increases, indicating that the confidence circuit 54 has more confidence in the reliability of the wear metal sensor 22 readings as the engine 14 approaches a steady operating efficiency.

In yet further embodiments, the confidence parameter is calculated or determined based on a combination of the service timer value and the engine timer value, taking the lower of the two values as the confidence value for the engine system 10. The thinking is that there may be a brief increase in wear metal particle concentration just after starting the engine 14, even when the engine 14 is healthy, and as a result, the confidence circuit 54 may need to lower the confidence parameter and push the diagnostic threshold out for a brief period of time after startup in order to avoid a false fault. Because the engine timer value is set at zero when the engine 14 is started, in some embodiments, and the confidence parameter is set as the lower of the two timer values, then the confidence parameter, in those embodiments, is set at zero at engine start up, which will lead to an increase of the diagnostic threshold for a period of time (via the dynamic threshold circuit). By increasing the diagnostic threshold at engine start up, the controller 26 avoids a situation in which a spike of wear metal particle concentration at engine 14 startup (which is expected, in part. due to an amount of wear metal particles that had settled when the engine 14 was off being sent through the engine system 10 all at once) would trigger a false fault.

The baselining circuit 56 is structured to filter out a standard, or nominal, version of a signal readout from the wear metal sensor 22 from the currently measured version in order to more accurately determine a significant change in wear metal particle flow (i.e., a filtered concentration of wear metal particles). Because small particles may travel through the engine system 10 without issues, removing those small particles from the reading allow more attention to be paid to the data that directly impact the engine system 10. The baselining circuit 56 may determine, i.e. 'learn,' the nominal level of wear metal particle flow by analyzing wear metal particle flow concentrations from the concentration circuit 52 and/or past particle flow values accessed from the memory device 38 to calculate an expected level of wear metal particle flow. In some embodiments, the baselining circuit 56 may take into account the calculated confidence parameter from the confidence circuit 54 by altering the refresh rate for the nominal flow level i.e. use a different time constant for the filter. This means that a low confidence value from the confidence circuit 54 would lead the baselining circuit 56 to update its nominal level value more often in order to map more closely with the predicted variability. On the other hand, when the confidence value from the confidence circuit 54 is high, the baselining circuit 56 may not update its nominal level value as frequently because it is not expecting variability in flow.

After learning the nominal flow level, the baselining circuit 56 applies the nominal flow level as a filter to the currently measured wear metal flow concentration from the concentration circuit 52, creating a filtered flow level that captures the deviation of the currently measured wear metal flow concentration from the nominal (i.e. expected) flow level. Then, the baselining circuit 56 compares the current wear metal flow concentration calculated by the concentration circuit 52 and measured by the wear metal sensor 22 with filtered flow level and calculates an instantaneous concentration deviation rate that captures flow aberrations in real-time. In some embodiments, the baselining circuit 56 applies this process to each bin as created by the concentration circuit 52, calculating an instantaneous concentration deviation rate for each bin.

The dynamic threshold circuit 58 is structured to adjust the diagnostic breaking point at which a sensor output value is deemed excessive. Generally, these diagnostic breaking points, or thresholds, are static and preset to a certain value. When the signal reading grows in value to be higher than the threshold, the exceedance can be recognized and used to determine whether an alert should be raised. When these thresholds are static, the thresholds are set with enough margin relative to 'healthy' behavior such that unaccounted—for noises, like transients, unexpected environmental conditions, and system behavior after parts replacement, can be ignored. However, there is a natural tension in the use of such a static diagnostic. Sufficient sensitivity is required to sense an 'unhealthy' behavior, which would tend toward a need to set the threshold as close as possible to 'healthy,' but tight thresholds are, predictably, subject to increased risk from disruption by noise and subsequent false faults. On the other hand, if the threshold is set more loosely in order to eliminate the effect of noise, the diagnostic system may fail to detect a failure or aberration.

In order to address these concerns, the dynamic threshold circuit 58 receives input primarily from the confidence circuit 54 and baselining circuit 56 to calculate a diagnostic threshold that captures 'unhealthy' behavior in the engine system 10 while minimizing false faults. If the dynamic threshold circuit 58 receives a low confidence value from the confidence circuit 54 and a high concentration deviation rate from the baselining circuit 56, as might be expected at initial ignition, it sets a high diagnostic threshold in order to ignore noise. Then, as the confidence value is increased and the concentration deviation rate decreases, as would be expected by having the engine 14 run, the dynamic threshold circuit 58 reduces the diagnostic threshold in order to monitor the now-more predictable process more closely. In this way, the dynamic threshold circuit 58 rejects noise when confidence in the wear metal sensor 22 readouts is low and then makes the diagnostic more sensitive to failures when confidence is high.

The alert circuit 60 is structured to monitor instances of failures and exceedances in light of the diagnostic thresholds set by the dynamic threshold circuit 58 and determine whether to raise an alert. When the concentration deviation of a bin gets above the instantaneous value of the diagnostic threshold set for that bin, the exceedance is noted and cataloged by the alert circuit 60. In some embodiments, the alert circuit 60 reacts to every instance of exceedance and raises an alert any time the diagnostic threshold is exceeded. In other embodiments, the alert circuit 60 feeds the exceedances into an accumulated sum, i.e. 'Cusum,' function, which serves to absorb noise. The Cusum function totals the exceedances over a period of time and triggers an alert if the total exceedances themselves exceed an established threshold. This function operates like a bucket: if the bucket fills up with exceedances in a certain period of time, then the bucket overflows and an alert is triggered. By utilizing a Cusum function in these embodiments, the alert circuit 60 ignores small exceedances which last for a short timeframe in order to avoid false faults and signal fatigue for the operators. For example, when a new lubrication pump 16 is installed, the lubrication pump 16 may have sharp edges on its machined surfaces that may cause metallic particles to be introduced into the lubrication system 18. Over time, the lubrication pump 16 will 'break in' and stop or reduce releasing such particles. By utilizing a Cusum function, the alert circuit 60 avoids overreacting to the initial lubrication pump 16 installation and causing a needless interruption. In some embodiments, different bins may be assigned different weights in the Cusum function of the alert circuit 60 such that exceedances in certain bins are treated as more important and will trigger an alert more quickly and with fewer overall exceedances than exceedances from less-weighted bins.

The notification circuit 62 is further structured to receive the alert status from the alert circuit 60 and provide an alert signal to the user interface 70 via the communications interface 66. In some embodiments, the alert signal prompts an audio, visual, or audio-visual alert that is observable by a user of the engine 14 and instructs the user that the concentration of wear metal particles in the lubricant flow has reached excessive levels. In some embodiments, the alert signal prompts only an audio or only a visual indication via the user interface 70. In other embodiments, the notification circuit 62 is structured to operate in a cloud-based computing environment (or another networked computing environment) such that the alert signal may be received by a remote operator. Further, the incorporation of the notification circuit 62 into the cloud enables remote monitoring of the vehicle by non-driver users, such as a service center or technician hub, which provides a technological improvement by connecting the users performing service on the vehicle (i.e. those users at the service center or technician hub) with real-time performance information on the vehicle and the engine 14.

In some embodiments, the notification circuit 62 is structured to receive the alert status from the alert circuit 60 and communicate with the controller 26 to de-rate or shutdown the engine 14 in order to avoid damage caused by excessive levels of wear metal particle concentration in the lubricant. De-rating refers to a forced limit on the engine 14 that temporarily caps the maximum energy output possible in order to protect the engine 14 and reduce the overall load on the engine 14. By working directly with the controller 26 and engine 14, the notification circuit 62 can automatically take steps to protect the engine 14 without relying on human input and activity.

Figure 4:
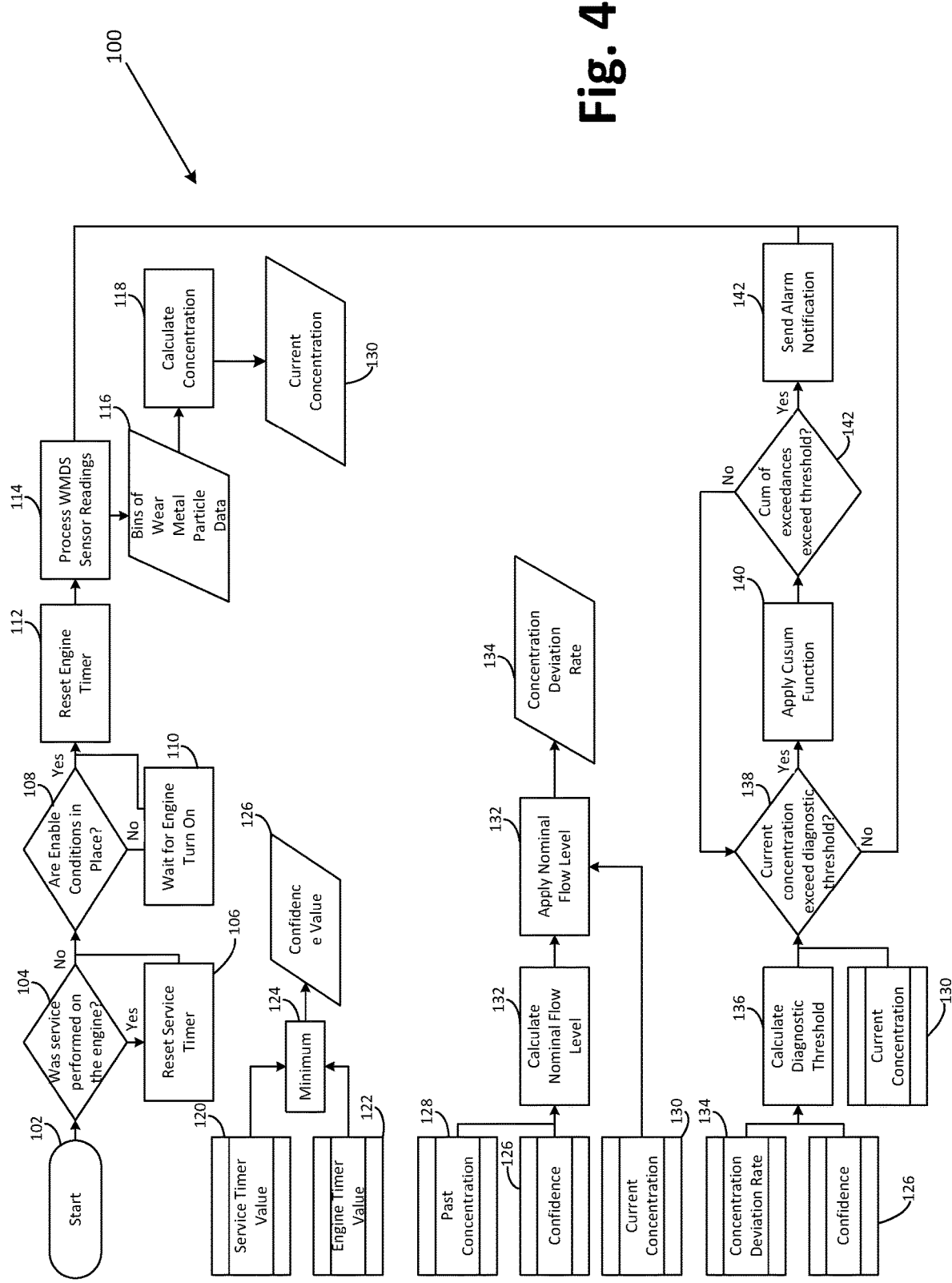
FIG. 4 is a flow diagram of a method of operating the engine system of FIGS. 1 and 2 according to an example embodiment.

Referring now to FIG. 4, a method 100 for monitoring wear metal particle concentration in the lubricant of an engine system is shown, according to an example embodiment. The method 100 starts at 102 and continues at step 104 where the controller checks if service was performed on the engine 14. If yes, the controller resets the service timer back to zero at step 106 and then goes to step 108. If no, the controller goes straight to step 108 and checks if the enable conditions are in place. If no, the controller waits until the engine 14 has been turned on at step 110 and then goes to step 112. If yes, the controller 26 proceeds directly to step 112 and resets the engine timer to zero.

Once the engine 14 has been started at step 112, the controller 26 (via the concentration circuit 52) receives and processes inputs from the wear metal sensor 22 at step 114, which are sorted into groupings at step 116. These groupings may be into bins based on size of the wear metal particles, type of the wear metal particles (i.e. ferrous or non-ferrous), or a combination of the two. At step 118, the controller 26 (via the concentration circuit 52) determines the concentration of wear metal particles by dividing the count of wear metal particles in each bin by a measured volume of lubricant that passed through the wear metal sensor 22, which is output at step 130 as the current concentration.

The controller 26 (via the confidence circuit 54) receives a value from the service timer at step 120 and a value from the engine timer at 122. At step 124, the controller 26 (via the confidence circuit 54) takes, chooses, or selects the minimum of the two values, which is output as the confidence value at step 126. Then, the controller 26 (via the baselining circuit 56) receives the confidence value from step 126 and the past concentration values from the memory device 38 at step 128. Taking these two inputs, the controller 26 (via the baselining circuit 56) calculates or determines a nominal flow level at step 132, which is then applied to the current concentration from step 130 at step 132 to calculate an instantaneous concentration deviation rate at step 134. The nominal flow may be based on the flow rate for a past predefined time period or other selected interval. In another embodiment, the nominal flow value is predefined within the controller.

The controller 26 (via the dynamic threshold circuit 58) then takes the instantaneous concentration deviation rate from step 134 and the confidence value from step 126 and calculates a diagnostic threshold at step 136. At step 138, the controller 26 (via the alert circuit 60) compares the current concentration from step 130 to the diagnostic threshold from step 136 at step 138. In one embodiment, if the current concentration does not exceed the diagnostic threshold, the controller 26 (via the alert circuit 60) does nothing and the process returns to step 114. If the current concentration does exceed the diagnostic threshold, the controller 26 (via the alert circuit 60) applies a cumulative summation (Cusum) function at step 140 by tracking and adding together each instance at which the current concentration exceeded the diagnostic threshold. The controller 26 (via the alert circuit 60) then checks if the output from the Cusum function at step 140 exceeds the cumulative threshold at step 142. If no, the controller 26 (via the alert circuit 60) does nothing and the process returns to step 138. If yes, the controller 26 (via the alert circuit 60) issues an alert response, which is sent as an alert notification by the controller 26 (via the notification circuit 62) at step 142.

Put differently, the controller 26 analyzes the flow of wear metal particles and, after filtering for the expected flow rate, compares the flow rate against a diagnostic threshold determined based in part on the determined confidence by the controller 26 in the reliability of the measurement of the flow. The exceedances are tallied by a Cusum function, and the controller 26 triggers an alert or takes protective action for the engine 14 if the metaphorical Cusum bucket overflows.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using one or more separate intervening members, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic. For example, circuit A communicably "coupled" to circuit B may signify that the circuit A communicates directly with circuit B (i.e., no intermediary) or communicates indirectly with circuit B (e.g., through one or more intermediaries).

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

While various circuits with particular functionality are shown in FIG. 1-4, it should be understood that the controller 26 may include any number of circuits for completing the functions described herein. For example, the activities and functionalities of the concentration circuit 52, the confidence circuit 54, the baselining circuit 56, the dynamic threshold circuit 58, the alert circuit 60, and the notification circuit 62 may be combined in multiple circuits or as a single circuit. Additional circuits with additional functionality may also be included. Further, the controller 26 may further control other activity beyond the scope of the present disclosure.

As mentioned above and in one configuration, the "circuits" may be implemented in machine-readable medium for execution by various types of processors, such as the processor 34 of FIG. 3. An identified circuit of executable code may, for instance, comprise one or more physical or logical blocks of computer instructions, which may, for instance, be organized as an object, procedure, or function. Nevertheless, the executables of an identified circuit need not be physically located together, but may comprise disparate instructions stored in different locations which, when joined logically together, comprise the circuit and achieve the stated purpose for the circuit. Indeed, a circuit of computer readable program code may be a single instruction, or many instructions, and may even be distributed over several different code segments, among different programs, and across several memory devices. Similarly, operational data may be identified and illustrated herein within circuits, and may be embodied in any suitable form and organized within any suitable type of data structure. The operational data may be collected as a single data set, or may be distributed over different locations including over different storage devices, and may exist, at least partially, merely as electronic signals on a system or network.

While the term "processor" is briefly defined above, the term "processor" and "processing circuit" are meant to be broadly interpreted. In this regard and as mentioned above, the "processor" may be implemented as one or more processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

Embodiments within the scope of the present disclosure include program products comprising machine-readable media for carrying or having machine-executable instructions or data structures stored thereon. Such machine-readable media can be any available media that can be accessed by a computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions and arrangement of the embodiments without departing from the scope of the present disclosure as expressed in the appended claims.

Accordingly, the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A system comprising:
 a controller comprising at least one processor coupled to at least one memory storing instructions that, when executed by the at least one processor, cause the at least one processor to:
  determine a concentration of wear metal particles in a lubricant for an engine system;
  determine a filtered concentration of the wear metal particles using a baseline concentration of the wear metal particles, the baseline concentration representing a concentration of wear metal particles having sizes below a size threshold;
  set a diagnostic threshold based on the filtered concentration of the wear metal particles; and
  responsive to determining that the concentration of the wear metal particles exceeds the diagnostic threshold, provide a notification.

2. The system of claim 1, wherein determining that the concentration of the wear metal particles exceeds the diagnostic threshold is based on a cumulative summation function that totals a plurality of exceedances, the plurality of exceedances regarding each instance that the concentration of the wear metal particles exceeds the diagnostic threshold.

3. The system of claim 1, wherein the instructions, when executed by the at least one processor, further cause the at least one processor to de-rate an engine of the engine system responsive to determining that the concentration of the wear metal particles exceeds the diagnostic threshold.

4. The system of claim 1, wherein in determining the concentration of the plurality of wear metal particles in the lubricant, the instructions, when executed by the at least one processor, further cause the at least one processor to:
 divert a portion of the lubricant from a lubricant flow to one or more sensors;
 determine one or more properties of the wear metal particles via the one or more sensors;
 determine the concentration of the wear metal particles based on the one or more properties; and
 return the portion of the lubricant to the lubricant flow.

5. The system of claim 4, wherein in determining the concentration of the wear metal particles based on the one or more properties, the instructions, when executed by the at least one processor, further cause the at least one processor to:
 sort the wear metal particles into one or more bins of wear metal particles based on the one or more properties; and
 determine a concentration for each of the one or more bins of wear metal particles.

6. The system of claim 4, wherein the portion of the lubricant is directed from the one or more sensors to an engine of the engine system.

7. The system of claim 4, wherein the portion of the lubricant is directed from the one or more sensors to a lubrication collector.

8. The system of claim 4, wherein the one or more sensors include at least one of:
 a particle sensor;
 an inductive proximity sensor; or
 a flow sensor.

9. A method comprising:
 determining, by a controller, a concentration of wear metal particles in a lubricant for an engine system;
 determining, by the controller, a filtered concentration of the wear metal particles using a baseline concentration of the wear metal particles, the baseline concentration representing a concentration of wear metal particles having sizes below a size threshold;
 setting, by the controller, a diagnostic threshold based on the filtered concentration of the wear metal particles; and
 providing, by the controller, a notification responsive to determining that the concentration of the wear metal particles exceeds the diagnostic threshold.

10. The method of claim 9, wherein determining that the concentration of the wear metal particles exceeds the diagnostic threshold is based on a cumulative summation function that totals a plurality of exceedances, the plurality of exceedances regarding each instance that the concentration of the wear metal particles exceeds the diagnostic threshold.

11. The method of claim 9, further comprising responsive to determining that the concentration of the wear metal particles exceeds the diagnostic threshold, de-rating, by the controller, an engine of the engine system.

12. The method of claim 9, wherein determining the concentration of the wear metal particles in the lubricant further comprises:
 diverting a portion of the lubricant from a lubricant flow to one or more sensors;
 determining, by the controller, one or more properties of the wear metal particles via the one or more sensors; and determining, by the controller, the concentration of the wear metal particles based on the one or more properties.

13. The method of claim 12, wherein determining the concentration of the wear metal particles based on the one or more properties further comprises:
sorting the wear metal particles into groupings based on the one or more properties; and
determining, by the controller, a concentration for each of the groupings of the wear metal particles.

14. The method of claim 12, further comprising:
directing the portion of the lubricant from the one or more sensors to an engine of the engine system; or
directing the portion of the lubricant from the one or more sensors to a lubrication collector.

15. The method of claim 12, wherein the one or more sensors include at least one of:
a particle sensor;
an inductive proximity sensor; or
a flow sensor.

16. A controller for an engine system, the controller comprising:
a processing circuit having at least one processor coupled to at least one memory device, the processing circuit configured to:
determine a concentration of wear metal particles in a lubricant for the engine system;
determine a filtered concentration of the wear metal particles using a baseline concentration of the wear metal particles, the baseline concentration representing a concentration of wear metal particles having sizes below a size threshold;
set a diagnostic threshold for the wear metal particles based on the filtered concentration of the wear metal particles; and
provide a notification based on determining that the concentration of the wear metal particles exceeds the diagnostic threshold.

17. The controller of claim 16, wherein the processing circuit is further configured to determine that the concentration of the wear metal particles exceeds the diagnostic threshold based on a cumulative summation function that totals a plurality of exceedances, the plurality of exceedances regarding each instance that the concentration of the wear metal particles exceeds the diagnostic threshold.

18. The controller of claim 16, wherein the processing circuit is further configured to, responsive to determining that the concentration of the wear metal particles exceeds the diagnostic threshold, de-rate an engine of the engine system.

19. The controller of claim 16, wherein in determining the concentration of the wear metal particles in the lubricant, the processing circuit is configured to:
cause a diversion of a portion of the lubricant from a lubricant flow to a plurality of sensors;
determine one or more properties of the wear metal particles via the plurality of sensors;
determine the concentration of the wear metal particles based on the one or more properties; and
cause the portion of the lubricant to be directed to an engine of the engine system or to a lubricant collector.

20. The controller of claim 19, wherein the one or more sensors include at least one of:
a particle sensor;
an inductive proximity sensor; or
a flow sensor.

* * * * *